(12) United States Patent
Koyama et al.

(10) Patent No.: US 8,802,428 B2
(45) Date of Patent: Aug. 12, 2014

(54) METHOD OF DETECTING MICROORGANISMS AND MICROORGANISM DETECTING APPARATUS

(75) Inventors: Mitsuaki Koyama, Sayama (JP); Shunichi Wakamatsu, Sayama (JP); Wakako Shinobu, Sayama (JP)

(73) Assignee: Nihon Dempa Kogyo Co., Ltd., Tokyo (JP)

( * ) Notice: Subject to any disclaimer, the term of this patent is extended or adjusted under 35 U.S.C. 154(b) by 0 days.

(21) Appl. No.: 12/931,790

(22) Filed: Feb. 10, 2011

(65) Prior Publication Data

US 2011/0223620 A1  Sep. 15, 2011

(30) Foreign Application Priority Data

Mar. 10, 2010  (JP) .................................. 2010-053586
Jul. 26, 2010  (JP) .................................. 2010-167194

(51) Int. Cl.
*G01N 33/53* (2006.01)
*G01N 33/567* (2006.01)
*G01N 5/02* (2006.01)

(52) U.S. Cl.
CPC ........................................ *G01N 5/02* (2013.01)
USPC .................. 435/288.7; 435/283.1; 435/287.1; 435/7.1; 435/7.2; 436/518; 436/525; 422/50; 422/82.01

(58) Field of Classification Search
CPC ........................................................ G01N 5/02
USPC .................. 435/283.1, 287.1, 288.7, 7.1, 7.2; 436/518, 525; 422/50, 82.01
See application file for complete search history.

(56) References Cited

U.S. PATENT DOCUMENTS

| | | | |
|---|---|---|---|
| 6,872,522 B1 | 3/2005 | Mecklenburg et al. | |
| 7,814,652 B2 * | 10/2010 | Bellew et al. | 29/854 |
| 8,236,508 B2 * | 8/2012 | Mutharasan et al. | 435/7.1 |
| 2003/0036644 A1 * | 2/2003 | Ulrich | 536/23.1 |
| 2005/0197495 A1 * | 9/2005 | Naidu | 530/400 |

(Continued)

FOREIGN PATENT DOCUMENTS

| | | |
|---|---|---|
| CN | 1243573 | 2/2000 |
| CN | 1584579 | 2/2005 |

(Continued)

OTHER PUBLICATIONS

Zhou et al. The Quartz Crystal Microbalance as a Continuous Monitoring Tool for the Study of Endothelial Cell Surface Attachment and Growth, 2000, Biotechnology Progress, vol. 16, pp. 268-277.*

(Continued)

*Primary Examiner* — Melanie Y Brown
(74) *Attorney, Agent, or Firm* — Jordan and Hamburg LLP

(57) ABSTRACT

It is possible to determine the presence of bacteria in a sample solution in a shorter period of time without changing a conventional incubating method. Bacteria in a sample solution are incubated in, for example, a sterilized agar medium 10 having a layer thickness of 0.1 μm to 1 μm formed on an electrode of a crystal resonator 2, and an oscillation frequency is measured. When the bacteria proliferate, the mass of the entire crystal resonator 2 increases, and the oscillation frequency decreases. Therefore, by monitoring presence of such a change over time, presence of bacteria in the sample solution can be determined quickly.

5 Claims, 13 Drawing Sheets

(56) References Cited

U.S. PATENT DOCUMENTS

| | | | |
|---|---|---|---|
| 2009/0291509 A1* | 11/2009 | Wakamatsu | 436/543 |
| 2010/0021346 A1* | 1/2010 | Wakamatsu et al. | 422/69 |
| 2010/0184200 A1* | 7/2010 | Yan et al. | 435/287.1 |

FOREIGN PATENT DOCUMENTS

| | | |
|---|---|---|
| EP | 0 938 143 | 8/1999 |
| JP | H03-257346 | 11/1991 |
| JP | H03-122565 | 12/1991 |
| JP | 2000-513436 | 10/2000 |
| JP | 2001-188068 | 7/2001 |
| JP | 2004-028594 | 1/2004 |
| JP | 2005-502313 | 1/2005 |
| JP | 2005-164495 | 6/2005 |
| JP | 2006-033195 | 2/2006 |
| JP | 2007-108170 | 4/2007 |
| JP | 2009-281744 | 12/2009 |
| WO | WO-97/49989 | 12/1997 |
| WO | WO-2005/001440 | 1/2005 |

OTHER PUBLICATIONS

Biosensors & Bioelectronics, 1996, vol. 11, No. 12, p. 11-93-1198 A rapid method for determination of *Proteus vulgaris* with a piezoelectric quartz crystal sensor coated with a thin liquid film Lili Bao, Le Deng, Llhua Nie, Shouzhuo Yao & Wanzhi Wei Department of Chemistry and Chemical Engineering, Hunan University, Changsha 410082, China (Received Nov. 12, 1995; accepted Jun. 5, 1996) pp. 1193-1198.

Analytica Chimica Acta, 1996, vol. 319, p. 97-101 Determination of microorganisms with a quartz crystal microbalance sensor Lili Bao, Le Deng, Lihua Nie, Shouzhuo Yao, Wanzhi Wei Department of Chemistry and Chemical Engineering, Hunan University, Changsha 410082, China Reeived Mar. 20, 1995; revised Sep. 14, 1995; accepted Sep. 16, 1995 pp. 97-101.

2008 IEEE International Frequency Control Symposium, 2008, p. 532-534 Examination for Realization of a High Precision Crystal Sensor Takeru Muto, Shigenori Watanabe, Shunichi Wakamatsu, and Mitsuski Koyama Nihon Dempa Kogyo Co., Ltd. 1275-2 Kamihirose, Sayama, Saitama, 350-1321, Japan.

* cited by examiner

Fig.11
(a) FRONT FACE
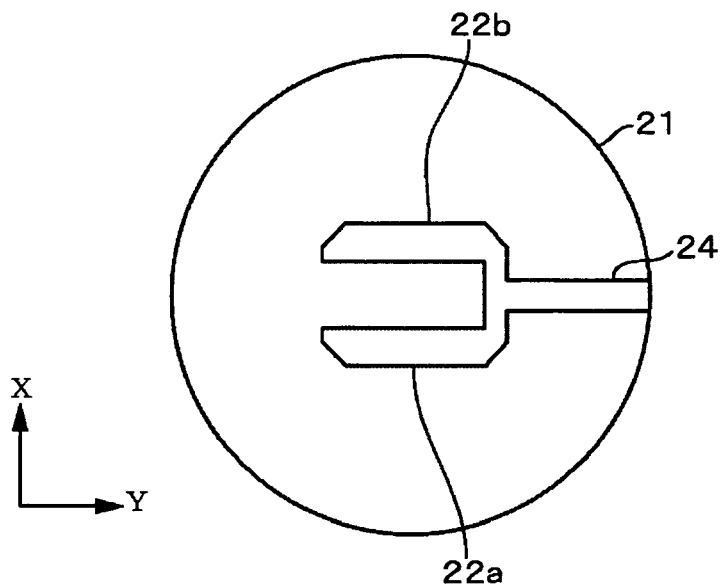
(b) REAR FACE
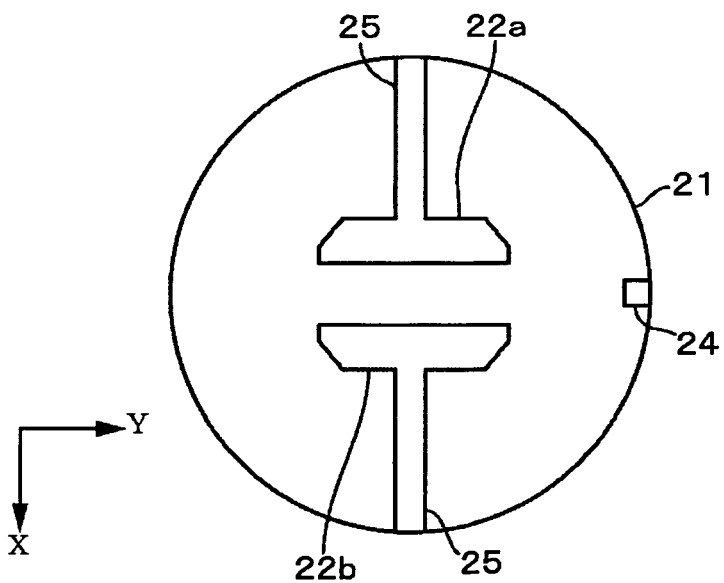

Fig.13
(a)
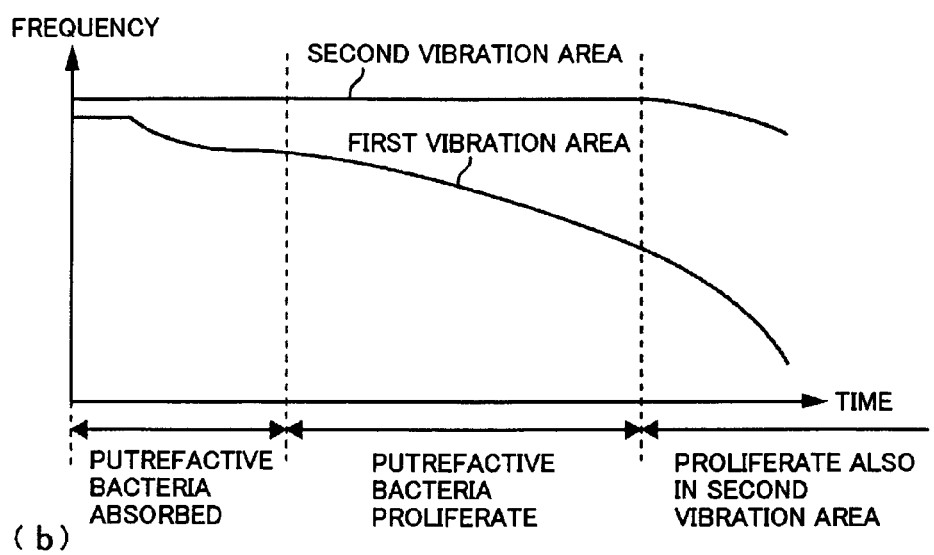
(b)
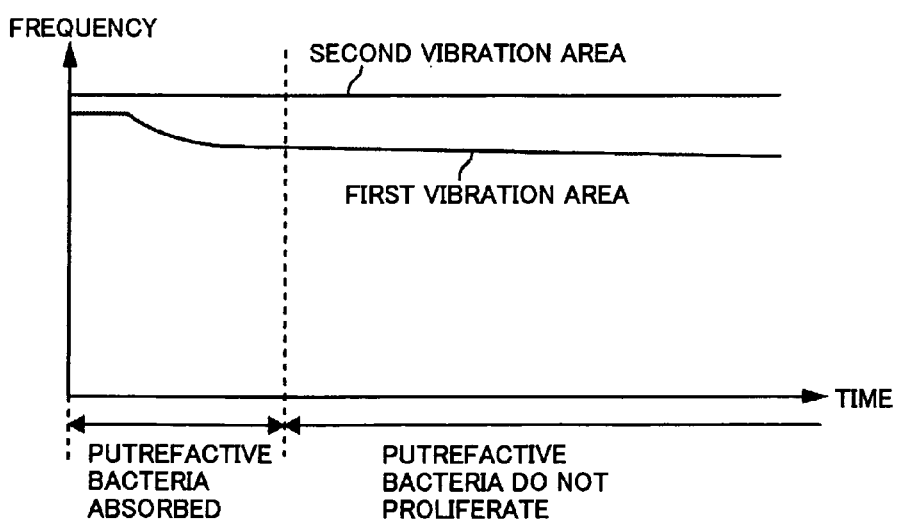

METHOD OF DETECTING MICROORGANISMS AND MICROORGANISM DETECTING APPARATUS

BACKGROUND OF THE INVENTION

1. Field of the Invention

The present invention relates to a method for detecting the presence of microorganisms such as bacteria and the rate of proliferation of microorganisms with a piezoelectric vibrator, and to a microorganism detecting apparatus.

2. Description of the Related Art

Nowadays, consciousness regarding food safety has been growing, and early detection of putrefactive bacteria which deteriorates food, beverage, and the like is an important issue.

Conventionally, as means for determining whether or not putrefactive bacteria are contained in food, beverage, or the like, there have been used measurement methods such as immuno assay, enzyme-linked immuno sorbent assay (ELISA), gas chromatograph/mass spectrometry (GC/MS), liquid chromatograph/mass spectrometry (LC/MS), and the like. However, pre-treatment in these methods are complicated, and it is hard to say that accuracy of determination is sufficient. Accordingly, a method to take long time to incubate putrefactive bacteria is common.

This incubation method is to incubate putrefactive bacteria which have a possibility to exist in a sample solution for two to four days at incubation temperatures from 30° C. to 60° C. for example, and then perform visual examination of a colony. However, it is difficult to apply this method to a subject of examination which needs to be determined in a short period, such as food and beverages, and thus there is a problem that shipment after a short period from manufacturing is not possible.

Translated National Publication of Patent Application No. 2000-513436 (claims 1, 7, and 15) describes a method for identifying a biological sample, and describes that components which coupled to a sensor array are determined directly by measuring increase in mass on a surface thereof, that a method for detecting increase in mass on the surface is to use a crystal oscillator balance, and that the biological sample is fungi, viruses, or bacteria. However, the present invention is not described in this publication.

SUMMARY OF THE INVENTION

The present invention is made in view of such situation, and it is an object thereof to provide a method capable of detecting the presence of microorganisms in a sample solution and the rate of proliferation of microorganisms easily and quickly by a shorter period of time.

The present invention is a method for detecting microorganisms including:

using a piezoelectric vibrator having electrodes formed on both faces and supplying a culture medium layer, which is an absorption layer formed on the electrode on one face side of the piezoelectric vibrator, with a sample solution in which it is possible that microorganisms which are detection targets are mixed; and oscillating the piezoelectric vibrator by an oscillation circuit and measuring an oscillation frequency of the piezoelectric vibrator, wherein at least one of presence of microorganisms and a rate of proliferation of microorganisms is obtained based on a change over time in the oscillation frequency.

Further, another invention is a method for detecting microorganisms including:

using a piezoelectric vibrator having electrodes formed on both faces and supplying the antibody layer, which is an absorption layer formed on the electrode on one face side of the piezoelectric vibrator, with a sample solution in which it is possible that microorganisms which are detection targets having an antigen to be absorbed in the antibody layer through antigen-antibody reaction are mixed;

supplying the antibody layer with a liquid culture medium; and oscillating the piezoelectric vibrator by an oscillation circuit and measuring an oscillation frequency of the piezoelectric vibrator, wherein at least one of presence of microorganisms and a rate of proliferation of microorganisms is obtained based on a change over time in the oscillation frequency.

Further, specific examples of the detecting methods are described below.

(a) the culture medium layer is a sterilized agar medium having a layer thickness of 0.1 μm to 1 μm.

(b) the piezoelectric vibrator includes a first vibration area for detecting microorganisms structured by forming electrodes on both faces of the piezoelectric vibrator, and a second vibration area for reference provided in an area different from the first vibration area via an elastic boundary layer and structured by forming electrodes on both faces of the piezoelectric vibrator, and the absorption layer is formed on the electrode on one face side of the first vibration area, but is not formed on either of the electrodes of the second vibration area.

(c) there is included displaying measurement values of the oscillation frequency as chronological data on a display unit.

(d) the measuring of a change over time in the oscillation frequency is performed in a state that a piezoelectric vibrator is placed in an incubation container at a constant temperature including a temperature adjusting part.

(e) the microorganisms are bacteria and fungi.

Still another invention is a detecting apparatus using a piezoelectric vibrator having electrodes formed on both faces, allowing microorganisms which are detection targets to be absorbed in an antibody layer formed on the electrode on one face side of the piezoelectric vibrator, and detecting detection targets by obtaining at least one of presence of microorganisms and a rate of proliferation of microorganisms based on a change over time in an oscillation frequency obtained from the piezoelectric vibrator, the detecting apparatus including:

an incubation container including an incubation space, to which a sample solution is supplied, for retaining a piezoelectric vibrator with a face on which the antibody layer is formed is directed to the incubation space;

a sample solution supply part supplying the incubation container with a sample solution in which it is possible that microorganisms which are detection targets having an antigen to be absorbed in the antibody layer through antigen-antibody reaction are mixed;

a culture medium supply part supplying the incubation container with a liquid culture medium; and an oscillation circuit for oscillating the piezoelectric vibrator.

Specific examples of the detecting methods are described below.

(f) the piezoelectric vibrator includes a first vibration area for detecting microorganisms structured by forming electrodes on both faces of the piezoelectric vibrator with the absorption layer being formed on the electrode on one face side thereof, and a second vibration area for reference provided in an area different from the first vibration area via an elastic boundary layer and structured by forming electrodes on both faces of the piezoelectric vibrator, where the absorption layer is not formed on either of the electrodes on the both faces, and wherein the detecting apparatus includes a first oscillation circuit oscillating the first vibration area and a second oscillation circuit oscillating the second oscillating area.

(g) the incubation container includes a temperature adjusting part for maintaining an incubation space at a constant temperature.

(h) the microorganisms are bacteria and fungi.

In the present invention, microorganisms in a sample solution is incubated in a culture medium formed on an electrode of a piezoelectric resonator, and proliferation of microorganisms is detected as a change in resonance frequency. Consequently, the presence of microorganisms and the rate of proliferation of microorganisms can be detected simply and quickly.

BRIEF DESCRIPTION OF THE DRAWINGS

FIG. 11 are plan views illustrating the crystal resonator and the wiring substrate which are used in the microorganism detecting apparatus;

FIG. 13 are characteristic charts illustrating examples of measurement results by the microorganism detecting apparatus.

DETAILED DESCRIPTION OF THE PREFERRED EMBODIMENTS

Figure 1:
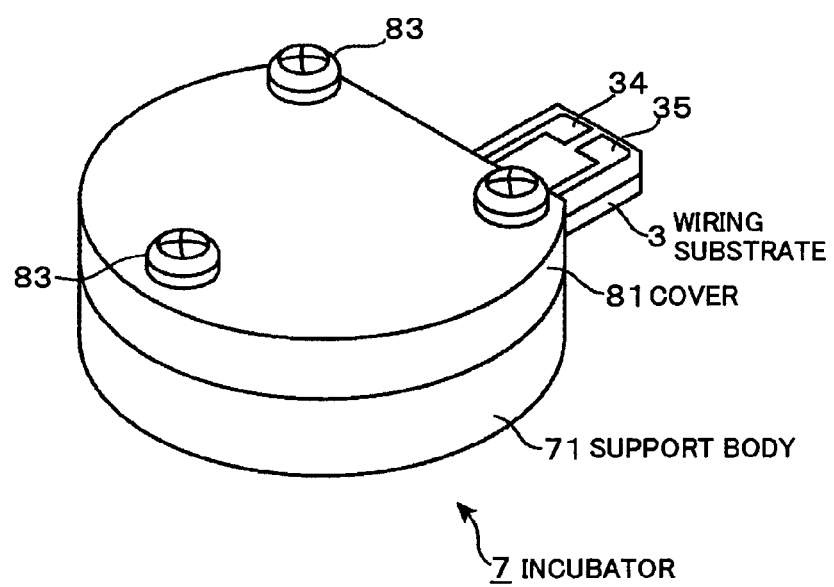
FIG. 1 is an external perspective view partially illustrating an incubation apparatus according to an embodiment of the present invention.
Figure 2:
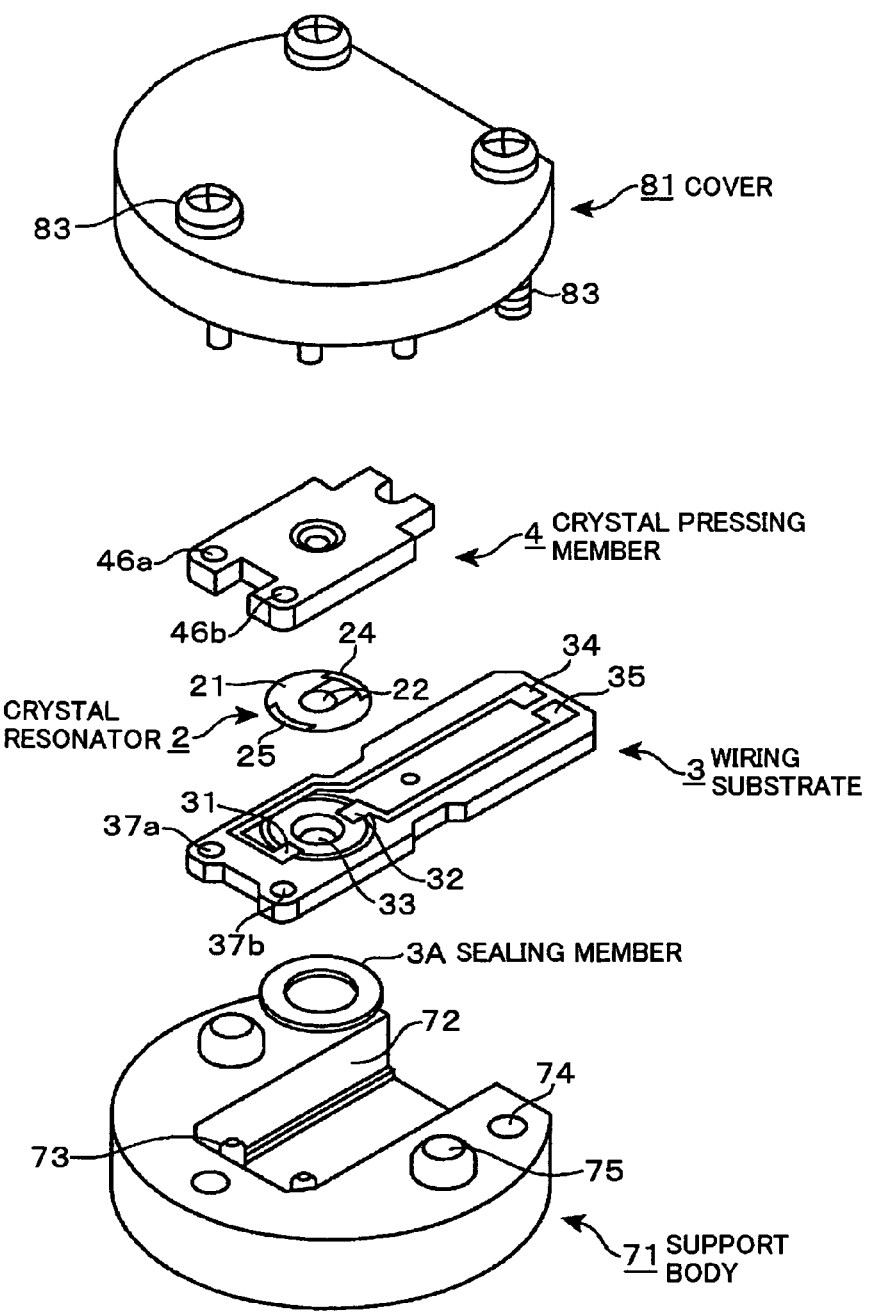
FIG. 2 is an exploded perspective view illustrating upper face sides of respective parts of the incubation apparatus.
Figure 3:
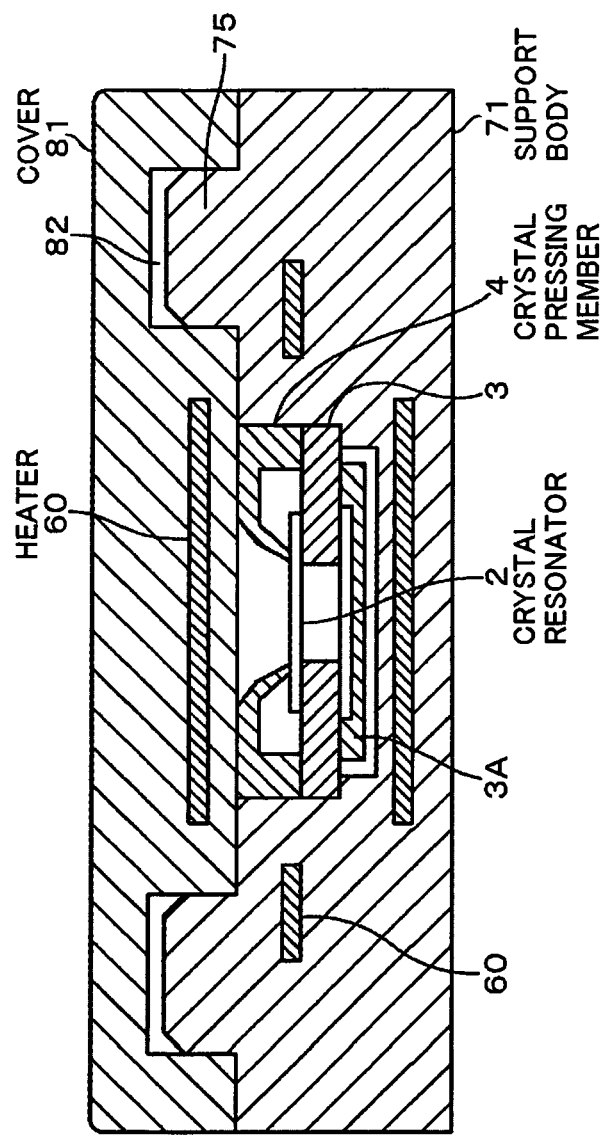
FIG. 3 is a vertical cross-sectional view illustrating the incubation apparatus.

An embodiment of a method for detecting microorganisms according to the present invention will be described with reference to the drawings. FIG. 1 and FIG. 2 are an external perspective view and an exploded perspective view, respectively, which partially illustrate an incubation apparatus used in this embodiment. Numeral 7 denotes an incubator (incubation container) which is formed of a support body 71 and a cover 81, and is structured of a sealing member 3A, a wiring substrate 3, a crystal resonator 2, and a crystal pressing member 4 which are stacked from a lower side in this order between the support body and the cover, as illustrated in FIG. 3.

The crystal resonator 2 which is a piezoelectric resonator is formed of a circular-shaped crystal piece 21, which is a piezoelectric piece, an excitation electrode 22, and lead-out electrodes 24, 25 (not illustrated in FIG. 4) as illustrated in FIG. 2. On a front face side of the crystal piece 21, the excitation electrode 22 in a foil shape is formed in a circular shape smaller in diameter than the crystal piece 21, and one end side of the lead-out electrode 24 in a foil shape is formed to be connected to the excitation electrode 22. This lead-out electrode 24 is bent along an end face of the crystal piece 21 and is routed to a rear face side of the crystal piece 21. On the other hand, also on the rear face side of the crystal piece 21, the excitation electrode 22 and the lead-out electrode 25 are formed to be connected in the same layout as the front face side. An equivalent thickness of the excitation electrode 22 and the lead-out electrodes 24, 25 is, for example, 0.2 μm, and gold, silver, or the like for example is used as a material for the electrodes.

Figure 4:
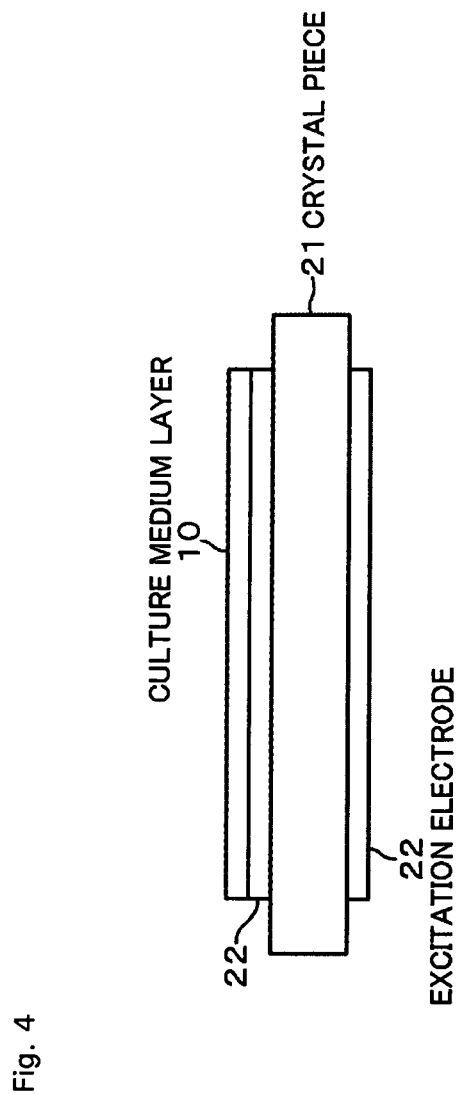
FIG. 4 is a vertical cross-sectional view schematically illustrating a crystal resonator on which a culture medium layer is formed on an upper face of an electrode, according to the embodiment of the present invention.

As illustrated in FIG. 4, on the excitation electrode 22 on the surface side (side to be in contact with a sample solution) provided on the crystal piece 21, there is formed a culture medium layer 10 which is an absorption layer to be an incubating environment for microorganisms, for example, bacteria such as putrefactive bacteria. As this culture medium layer 10, for example, a sterilized agar medium can be used. A layer thickness of this agar medium is, for example, 0.1 μm to 1 μm. This is because when the layer thickness is 0.1 μm or less, incubation of microorganisms is not possible, and when the layer thickness is more than 1 μm, the crystal resonator is not driven easily because the agar has high viscosity. A method for forming the culture medium layer 10 on the excitation electrode 22 is performed as follows for example. First, on both the front and rear faces of a crystal wafer, electrode patterns are formed at positions corresponding to the positions of forming numerous crystal pieces. Then, on a rotatable vacuum chuck (rotation stage including a vacuum absorbing function), this crystal wafer is held horizontally in a state that the center of the wafer and the center of rotation are aligned. A solution containing a culture medium which is adjusted to a predetermined agar concentration is supplied to the center of the wafer, and the spin chuck is rotated by a motor coupled to a rotation shaft of the spin chuck, thereby spreading the solution on the surface of the wafer to form a thin liquid film. The thickness of this liquid film can be adjusted according to the rotation speed, and thus by adjusting this rotation speed, the culture medium layer 10 having a layer thickness of 0.1 μm to 1 μm can be formed on the wafer. Thereafter, the wafer is divided by dicing to obtain individual pieces of crystal resonators. Although the culture medium layer 10 is drawn to be formed only on the excitation electrode in FIG. 4, the culture medium 10 is formed on the entire surface of the crystal piece by this spin coating method. Also in this case, by structuring such that the ratio of the area of the electrode to the area of the entire surface of the crystal piece is larger, the weight of the culture medium would not affect driving of the crystal resonator. An oscillation frequency of this crystal resonator at this point is assumed as a reference for detecting microorganisms. At this time, it is assumed that when the agar concentration is constant, viscosity resistance thereof is constant, and the Kanazawa-Gordon formula is used.

Referring back to FIG. 2, the wiring substrate 3 is formed of a printed circuit board for example, and electrodes 31, 32 are provided at an interval on a surface thereof. A through hole 33 for a recessed portion forming an air-tight space, in which the excitation electrode 22 on the rear face side of the crystal resonator 2 is exposed as will be described later, is formed between the electrodes 31, 32, and the through hole has a bore formed to have a size in which the excitation electrode 22 can be accommodated. On a rear end side of the wiring substrate 3, connection terminal parts 34, 35 are provided and connected electrically to the electrodes 31, 32, respectively, via conductive paths. The sealing member 3A is formed of a circular body with a recessed portion formed in a center portion, and has a role to block a lower face of the through hole 33 and form an air-tight space which is a rear side atmosphere of the crystal resonator 2. The lead-out electrodes 24, 25 of the crystal resonator 2 are connected electrically by a conductive adhesive.

The crystal pressing member 4 is made in a shape corresponding to the wiring substrate 3 using an elastic material, for example a silicone rubber. A lower face of the crystal pressing member 4 is, as illustrated in FIG. 3, formed so as to press a peripheral portion of the excitation electrode of the crystal resonator 2 against the support body 71 side. The crystal pressing member 4 has a role of pressing the crystal resonator 2 against an outside area of the through hole 33 formed in the wiring substrate 3, so that when the cover 81 is fitted with the support body 71, the crystal pressing member 4 presses the crystal resonator 2 and the wiring substrate 3 against the support body 71 side.

The cover 81 is positioned onto the support body 71 by engagement of recessed portions 82 formed in a lower face thereof and projections 75 formed on the support body 71 side as illustrated in FIG. 3, and is fixed by screws 83 which are screwed into holes 74 on the support body 71 side. A heater 60 which is a temperature adjusting part is provided in the cover 81 and the support body 71 which form the incubator 7, and by this heater 60 the atmosphere in which the culture medium layer is placed is set to an atmosphere at a preset temperature (constant temperature atmosphere).

In the support body 71, a recessed portion 72 in which the wiring substrate 3 is accommodated and retained is provided, and in this recessed portion 72, engaging projections 73 extend in a vertical direction and engage with engaging holes 37a, 37b of the wiring substrate 3 and engaging holes 46a, 46b of the crystal pressing member 4, thereby fixing positions of the wiring substrate 3 and the crystal pressing member 4.

Figure 6:
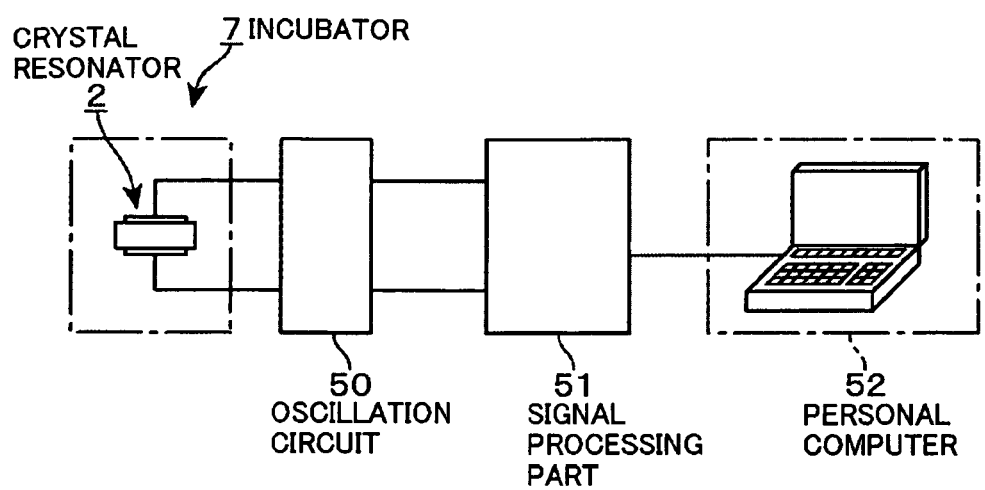
FIG. 6 is a diagram schematically illustrating the overall structure of the incubation apparatus.

Next, a circuit part and a signal processing part of the incubation apparatus will be described. In FIG. 6, numeral 50 denotes an oscillation circuit, numeral 51 denotes a signal processing part, and numeral 52 denotes a personal computer. A screen of this personal computer 52 constitutes a display unit.

The oscillation circuit 50 is connected electrically to the electrodes 34, 35 formed on the wiring substrate 3, and is provided on the support body 71 for example. The signal processing part 51 performs analog/digital conversion (A/D conversion) of a signal having a frequency from the oscillation circuit 50, and performs predetermined signal processing thereon to measure the frequency of the frequency signal.

Next, a process of detecting whether target bacteria are present in a sample solution or not using the thus structured incubation apparatus will be described. In this example, assuming that the bacteria are putrefactive bacteria, a filter which allows passing of the putrefactive bacteria is prepared, and a sample solution is made to pass through this filter. Then, the passed liquid is sampled with a dropper for example, dropped onto a surface of the culture medium layer 10 on the already-described crystal resonator 2 fitted in the support body 71, and spread thinly thereon. Thereafter, the cover 81 is fitted onto the support body 71, and the temperature in the incubator 7 (the temperature of the atmosphere in which the crystal resonator 2 is placed) is raised by the heater 60 to, for example, between 40° C. to 60° C., 45° C. in this example.

Figure 5:
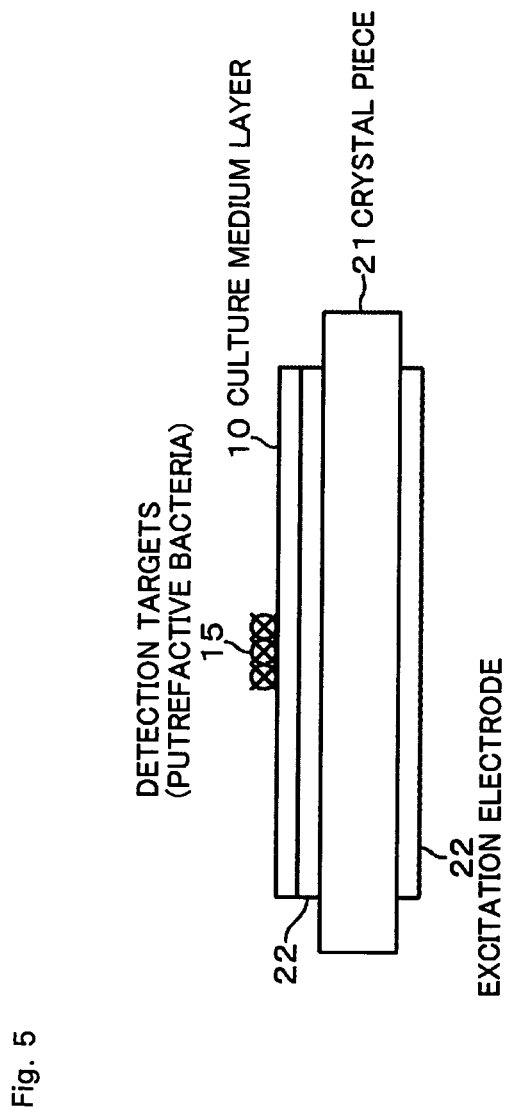
FIG. 5 is a vertical cross-sectional view schematically illustrating the crystal resonator in a state that microorganisms are incubated on a culture medium layer to which a sample solution is added.

Then the aforementioned atmosphere is kept airtight, and the sample solution on the culture medium layer 10 evaporates, thereby turning this atmosphere to a saturated steam atmosphere for example. On the other hand, measurement values of the oscillation frequency of the crystal resonator 2 are taken into the personal computer 52 chronologically, and these chronological data are displayed on the screen thereof. In the incubator 7, the total mass of the sample solution on the electrodes of the crystal resonator 2 and the culture medium layer 10 varies until water in the sample solution evaporates and saturates the atmosphere. However, once the saturated atmosphere is established, the total mass becomes table. Now, if putrefactive bacteria (detection targets 15) exist in the sample solution applied on the culture medium layer 10 as illustrated in FIG. 5, these bacteria take in nutriments in the culture medium layer and proliferate. Thus, the mass of a portion on the electrodes increases from the point when the proliferation starts, and the oscillation frequency increases. Accordingly, when it is configured to display the chronological data of the oscillation frequency on the screen of the personal computer 52 in the form of a graph for example, it is possible to allow recognition of existence of the putrefactive bacteria by, for example, visually detecting a rising of the oscillation frequency.

Further, by obtaining the degree of increase in oscillation frequency, the rate of proliferation of the putrefactive bacteria can be obtained. In this case, when the relation between the oscillation frequency and the mass of an object mounted on the electrode 22 of the crystal resonator 2 is obtained in advance, the rates of proliferation at predetermined time intervals can be obtained for example. Moreover, an air-pipe (air passage) and an exhaust pipe (exhaust passage) (not illustrated) which each communicate with the atmosphere are connected to the incubator 7, and air, for example dry air, is supplied in a state that the exhaust pipe is open, to thereby remove water on the crystal resonator 2 to some degree. Then, measurement of the oscillation frequency may be performed after air containing, for example, slightly less steam than the saturated steam atmosphere is sent in at the set temperature in the incubator 7, respective valves provided on the air-pipe and the exhaust pipe are closed, and water on the crystal resonator 2 evaporates slightly to cause the atmosphere to be saturated steam atmosphere.

Figure 7:
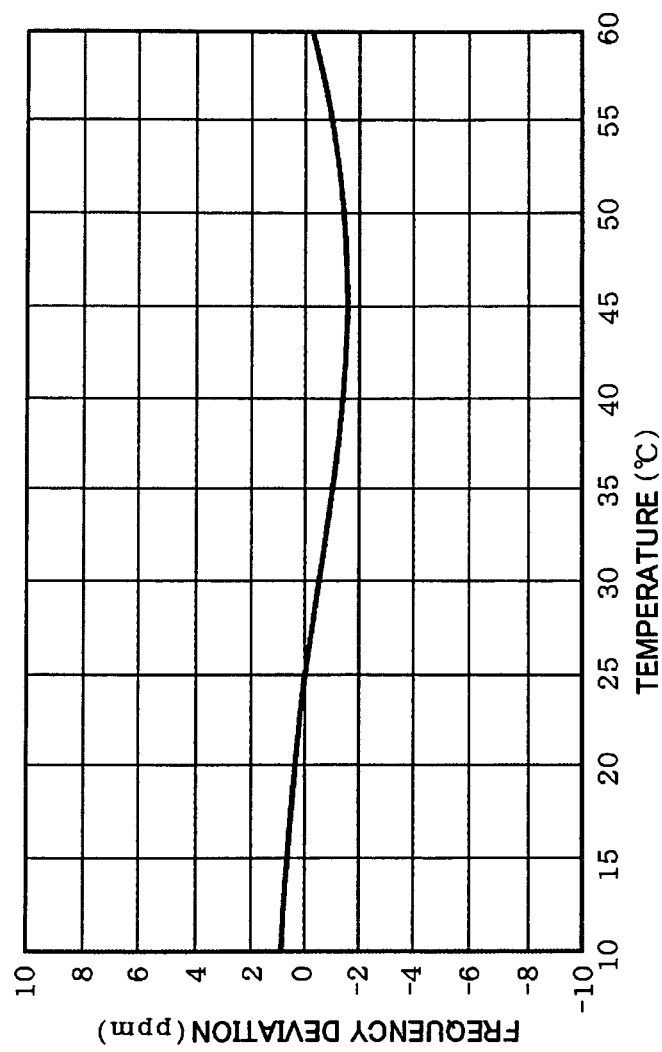
FIG. 7 is a characteristic chart illustrating an example of a frequency temperature characteristic of the crystal resonator.

In addition, it is preferred that the set value of the incubation temperature be a temperature at which a temperature characteristic of the frequency of the crystal resonator becomes most stable within the range of growth temperature of bacteria. FIG. 7 illustrates an example of a frequency temperature characteristic of an AT-cut crystal resonator. In this case, the temperature at which a frequency change amount per unit temperature change in the growth temperature range is smallest is 45° C., which is the temperature at the external value of the graph, and it is preferred that the incubation temperature is set to this temperature. For beverages, a sample solution can be prepared by just passing through the filter, but when the presence of putrefactive bacteria in food is checked, a sample solution can be prepared by incubating the putrefactive bacteria by a method based on an official method or by mixing the putrefactive bacteria directly with water and then passing this water through the filter.

In such a method for detecting bacteria, after a sample solution is dropped onto the culture medium layer 10 and the frequency becomes stable, the oscillation frequency starts to increase for example after a lapse of a few tens of minutes. Thus, the presence of bacteria can be detected by a short period of time, and hence whether the putrefactive bacteria are present in food or beverage can be detected quickly. Further, the operation is simple and the accuracy of measurement is high.

Note that in the present invention, microorganisms include bacteria fungi, and the like.

Figure 8:
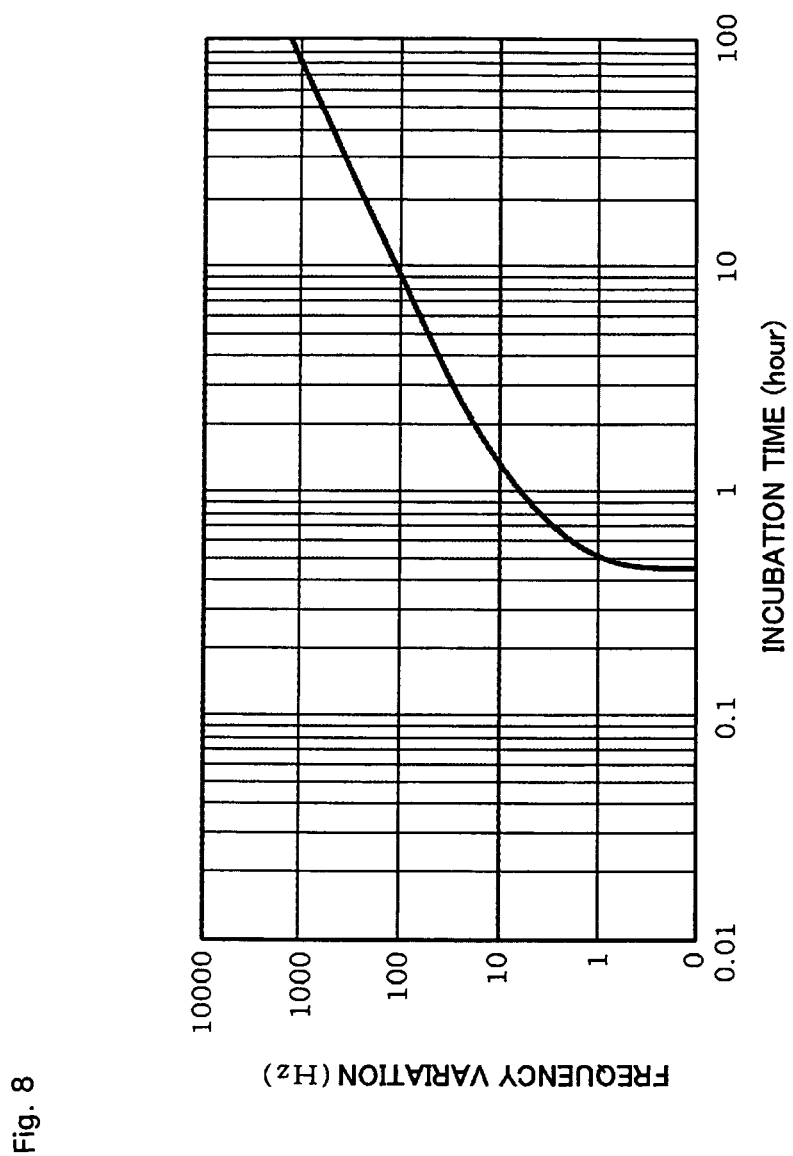
FIG. 8 is a characteristic chart illustrating an example of a measurement result by the incubation apparatus.

Using the above-described incubation apparatus, the sample solution containing putrefactive bacteria was adhered on the culture medium layer 10 of the crystal resonator 2 as already described, and after the oscillation frequency becomes table, a change over time of a frequency difference with respect to this frequency was measured. A measurement result is illustrated in FIG. 8. As the crystal resonator, an AT-cut crystal resonator having a diameter φ of 8.7 mm of 9 MHz (with an electrode diameter φ of 5.0 mm) is used, and measurement of frequency is performed at 10 mHz/sec. As a strain to be a detection target, a standard strain (ATCC49025) of *Alicyclobacillus acidoterrestris* is used, and this strain is incubated at 45 degrees Celsius in an agar medium on the crystal resonator with a layer thickness of 0.5 μm. Here, an yeast extract, glucose, several trace elements, and so on are added to this agar. As illustrated in FIG. 8, the frequency decreases by 1 Hz after about 0.5 hour from start of incubation, and the inherent frequency keeps decreasing thereafter. This is due to increase in mass caused by proliferation of the putrefactive bacteria, and from this increase, proliferation of the putrefactive bacteria can be confirmed. Here, as a device for detecting the frequency, a device sold by the applicant (NAPiCOS system, registered trademark) capable of measuring the frequency with quite high accuracy is used.

Further, by obtaining an analytical curve representing a relation between the weight and the oscillation frequency in advance, a frequency difference can be converted into a mass increase amount. Thus, the rate of change in mass at each incubation elapsed time, that is, the rate of proliferation of the detection target at each incubation elapsed time can be digitized.

Figure 9:
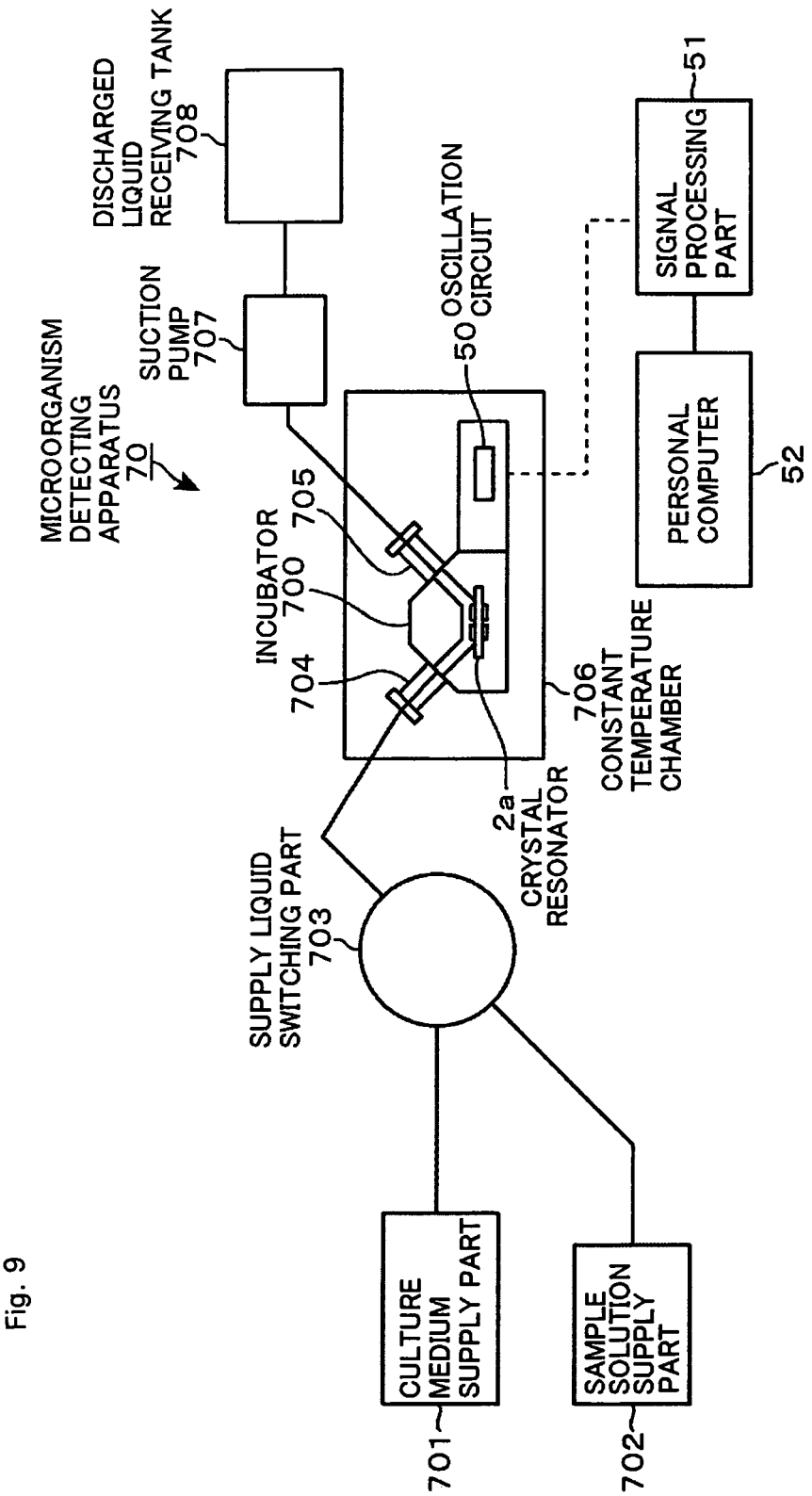
FIG. 9 is an explanatory diagram illustrating the structure of a microorganism detecting apparatus according to a second embodiment.

Next, a second embodiment of detecting microorganisms such as bacteria using an antibody will be described. A method for detecting microorganisms according to this example is different from the detecting method according to the first embodiment, in which the culture medium layer 10 is formed on the excitation electrode 22 to perform incubation, in that an antibody layer as an absorption layer is provided on the excitation electrode 22 of a crystal resonator 2a, and a culture medium solution (liquid culture medium) is supplied to the atmosphere in which this crystal resonator 2a is mounted, to thereby perform incubation of microorganisms. FIG. 9 illustrates the structure of a microorganism detecting apparatus 70 using the method for detecting microorganisms according to the second embodiment. In FIG. 9, components common to the first embodiment are given the same reference numerals as those in FIG. 1 to FIG. 6.

In the microorganism detecting apparatus 70 illustrated in FIG. 9, an incubator 700 is in common with the incubator 7 illustrated in FIG. 2 and FIG. 3 in that the crystal pressing member 4 and the sealing member 3A are used to retain the piezoelectric sensor constituted of the crystal resonator 2a and a wiring substrate 3a in the incubator 700. On the other hand, the incubator is different from the incubator 7 according to the first embodiment, in which a sample solution is applied on the culture medium layer 10 and this layer is disposed in a closed atmosphere, in that a supply port 704 for supplying a sample solution into the incubator 700 and a discharge port 705 for discharging a sample solution from inside the incubator 700 are provided on the cover 81 of the incubator 700, and a sample solution or culture medium solution can be supplied externally.

The supply port 704 of the incubator 700 is connected to a supply liquid switching part 703 including a not-illustrated sample loop which retains a sample solution and a culture medium solution temporarily while suppressing mixing of them and switching a connection destination of the supply port 704 between a culture medium solution supply part 701 constituted of a syringe pump retaining the culture medium solution and a sample solution supply part 702 constituted of a syringe retaining the sample solution, and so on. On the other hand, the discharge port 705 is connected to a discharged liquid receiving tank 708 via a suction pump 707, and this suction pump 707 is used to supply the culture medium solution and the sample solution to the incubator 700 and to discharge them therefrom.

Further, the incubator 700 according to this example is different from the first embodiment performing temperature adjustment using the heater 60 in that temperature adjustment of the atmosphere in which the crystal resonator 2a is disposed is performed by disposing the incubator in, for example, a hot-air type constant temperature chamber 706 together with the oscillation circuit 50 connected to the crystal resonator 2a.

Further, the point that the incubator is connected to the oscillation circuit 50 for the crystal resonator 2a and is connected to the personal computer 52 via the signal processing part 51 is the same as in the first embodiment illustrated in FIG. 6.

Figure 10:
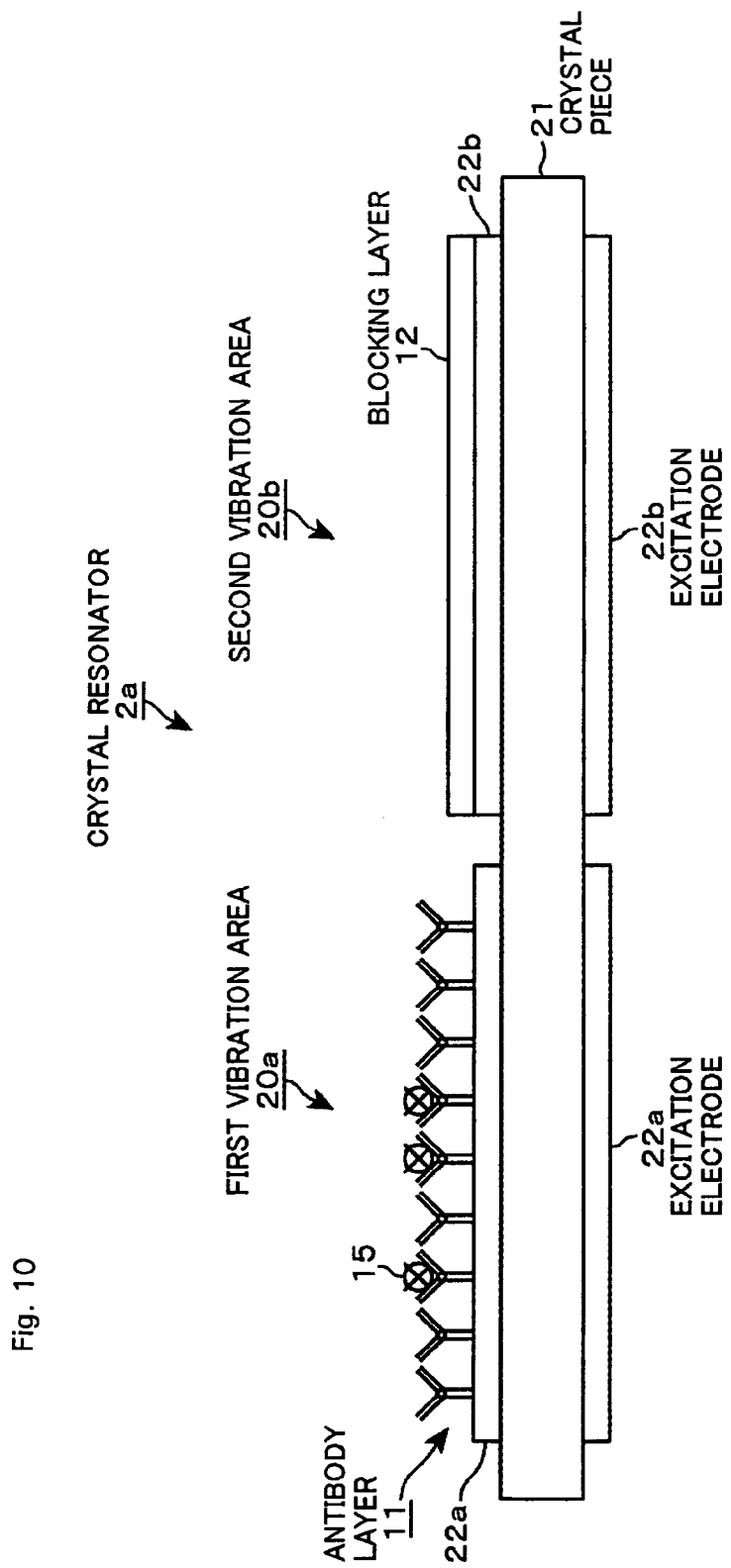
FIG. 10 is a schematic view illustrating the structure of a crystal resonator disposed in an incubator of the microorganism detecting apparatus.

Here, in the crystal resonator 2a according to this embodiment, two pairs of excitation electrodes 22a, 22b are provided on a front and rear faces of a crystal piece 21 as illustrated in FIG. 10, FIG. 11(a), and FIG. 11(b), and form a first vibration area 20a and a second vibration area 20b, respectively. On an upper face of the excitation electrode 22a on a front face side of the first vibration area 20a, there is formed an antibody layer 11 carrying an antibody assuming a membrane protein contained specifically in a surface of bacteria, which are the detection targets 15, as an antigen and reacting with this antigen, and the antibody layer forms a vibration area for detecting microorganisms where bacteria are made to be absorbed into the surface of the excitation electrode 22a. On the other hand, on the surface of the excitation electrode 22b of the second vibration region 20b, a blocking layer 12 constituted of a protein or the like which does not easily react with the antibody is formed, and the bacteria are not easily absorbed into the surface of the excitation electrode 22b. Accordingly, the second vibration area 20b forms a vibration area for reference to detect a change in oscillation frequency due to any other factor (for example, an environmental change which will be described later) which is not due to absorption of microorganisms.

Regarding fixing of the antibody to the excitation electrode 22a, for example, a reagent containing the antibody is supplied to an upper face side of the crystal resonator 2a on which the other excitation electrode 22b is masked in advance, to thereby form the antibody layer 11 on a surface of the exposed excitation electrode 22a. Formation of the blocking layer 12 on the other excitation electrode 22b is similarly performed by, for example, masking the excitation electrode 22a on which the antibody layer 11 is to be formed, and then making the other excitation electrode 22b to be in contact with a reagent containing a protein to be the blocking layer.

Figure 12:
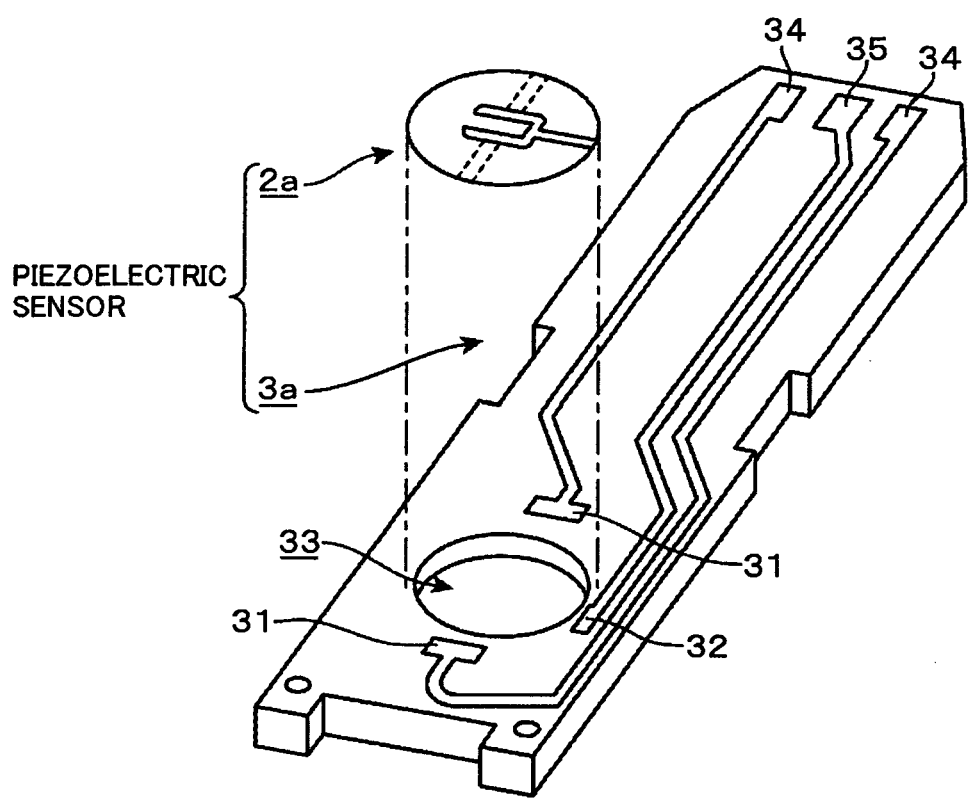
FIG. 12 is a perspective view illustrating a piezoelectric sensor including the crystal resonator.

As illustrated in FIG. 12, the crystal resonator 2a is disposed on the wiring substrate 3a capable of taking out oscillation frequencies separately from the first vibration area 20a and the second vibration area 20b, and the areas 20a, 20b are connected to separate oscillation circuits 50. In the example illustrated in FIG. 11 and FIG. 12, the excitation electrodes 22a, 22b on the front face side are led to a connection terminal part 35 via a common lead-out electrode 24 and an electrode 32 on the wiring substrate 3 side, and is connected to a ground line on the oscillation circuit 50 side. On the other hand, the excitation electrodes 22a, 22b on the rear face side are led to connection terminal parts 34 via separate lead-out electrodes 25 and electrodes 31 on the wiring substrate 3 side, and are connected to the respective independent oscillation circuits 50.

Spore forming bacteria, for example Clostridium perfringens, are able to proliferate under a relatively high temperature condition of, for example, 50° C. to 70° C., and become deterioration factors in food stored under such a temperature condition. Accordingly, when the spore forming bacteria are the detection targets 15, it is necessary to retain the crystal resonator 2a contacted with the sample solution under the same temperature condition as the storing condition of food, and measure the presence of bacteria to be absorbed in the antibody layer 11 and the presence of proliferation of bacteria. On the other hand, it is known that the oscillation frequency characteristic of the crystal resonator 2a changes according to a change in the ambient temperature, a change in viscosity of fluid, and the like (hereinafter referred to as environmental changes for convenience). However, it is difficult to discriminate by measurement in a short time whether a change in oscillation frequency is due to absorption of bacteria into the antibody layer 11 or due to a variation in temperature control and a change in viscosity of the surrounding fluid in the constant temperature chamber 706.

Accordingly, in the microorganism detecting apparatus 70 according to this embodiment, the first vibration area 20a provided with the antibody layer 11 which absorbs bacteria and the second vibration area 20b provided with the blocking layer 12 which does not absorb bacteria are disposed under the same environment. Thus, changes in oscillation frequency due to both the absorption of bacteria and the environmental changes are obtained from the first vibration area 20a, whereas changes in oscillation frequency only due to surrounding environmental changes and excluding absorption of bacteria can be obtained from the second vibration area 20b. Thus, by taking a difference between oscillation frequencies obtained respectively from the first and second vibration areas 20a, 20b, the influence of the environmental changes is removed from the oscillation frequency of the first vibration area 20a, and only the change in the oscillation frequency due to absorption of bacteria can be taken out.

Hereinafter, operation of the above-described microorganism detecting apparatus 70 will be described. First, a piezoelectric sensor is attached in the incubator 700, and the temperature in the constant temperature chamber 706 is set so that the ambient temperature of the incubator 700 and the oscillation circuit 50 becomes the storage temperature of food contained in a sample solution for example. When the temperature of the constant temperature chamber 706 becomes stable, the supply liquid switching part 703 is connected to the culture medium solution supply part 701 side and the suction pump 707 is activated, and a culture medium solution is filled as a supplied liquid buffer in the incubator 700 and pipes connected thereto. Then the oscillation circuit 50 is activated to start obtaining oscillation frequencies from the first, second vibration areas 20a, 20b.

Thereafter, the connection destination of the supply liquid switching part 703 is switched to the sample solution supply part 702 to supply the sample solution to the incubator 700, and the suction pump 707 is stopped once at the timing the inside of the incubator 700 is replaced with the sample solution. At this time, if the sample solution contains putrefactive bacteria such as spore-forming bacteria which undergo antigen-antibody reaction with the antibody of the antibody layer 11, the putrefactive bacteria are absorbed into the antibody layer 11, and the oscillation frequency of the first vibration area 20a lowers as illustrated in the period described as "putrefactive bacteria absorbed" in FIG. 13(a) and FIG. 13(b).

On the other hand, on the second vibration area 20b side where the blocking layer 12 is provided, absorption of the putrefactive bacteria hardly occurs, and thus there occurs no change in oscillation frequency in the aforementioned period. Here, for simplicity, in the examples illustrated in FIG. 13(a) and FIG. 13(b), the culture medium solution supplied from the culture medium solution supply part 701 and the sample solution supplied from the sample solution supply part 702 are adjusted in advance to almost the same temperature as the temperature in the incubator 700 which is adjusted in the constant temperature chamber 706. Further, it is assumed that the culture medium solution and the sample solution have substantially the same viscosity, and no change in oscillation frequency occurs due to switching between the culture medium solution and the sample solution.

Thus, when a predetermined time has passed and a time by which a sufficient amount of microorganisms can be absorbed in the antibody layer 11 has passed, the connection target of the supply liquid switching part 703 is switched again to the culture medium solution supply part 701, and then the suction pump 707 is activated so as to replace the inside of the incubator 700 with the culture medium solution. When the inside of the incubator 700 is thus brought to a state of being filled with the culture medium solution, the suction pump 707 is stopped again, and the inside of the incubator 700 is brought to a stationary state. Here, when the putrefactive bacteria absorbed into the antibody layer 10 are alive, the putrefactive bacteria receive nutriments from the culture medium solution and proliferate. The proliferation of the putrefactive bacteria at this time occurs near the surface of the antibody layer 11 where these putrefactive bacteria are absorbed. Thus, when the inside of the incubator 700 is in a stationary state, the proliferated putrefactive bacteria spread in the culture medium solution, and a part thereof is absorbed in the antibody layer 11.

As a result, as illustrated in the period described as "putrefactive bacteria proliferate" in FIG. 13(a), the oscillation frequency on the first vibration area 20a side decreases over time due to absorption of the proliferated putrefactive bacteria. On the other hand, on the second vibration area 20b side provided with the blocking layer 12, there is still almost no decrease in oscillation frequency. In these periods described as "putrefactive bacteria absorbed" and "putrefactive bacteria proliferate" in FIG. 13(a), when environmental changes, such as temperature changes and/or viscosity changes, occur inside the incubator 700, changes in oscillation frequency accompanying these environmental changes occur at substantially the same widths in the first, second vibration areas 20a, 20b placed at the common temperature and in the common culture medium solution atmosphere.

Accordingly, by taking the absolute value of the difference between the oscillation frequencies obtained from the first, second vibration areas 20a, 20b, the changes in oscillation frequency accompanying the environmental changes are cancelled out, and a change in oscillation frequency only due to absorption of the putrefactive bacteria can be taken out. Then, similarly to the first embodiment, the amount of absorbed putrefactive bacteria is recognized by using an analytical curve or the like indicating the relation between the weight of the putrefactive bacteria obtained in advance and the amount of decrease in oscillation frequency.

There may be a case where the amounts of changes in the oscillation frequencies of the first, second vibration areas 20a, 20b due to the environmental changes are not strictly equal. In this case, variations in the oscillation frequencies accompanying such environmental changes can be cancelled out properly by multiplying each of the oscillation frequencies with a proportionality constant obtained in advance to make the amounts of changes in oscillation frequency per unit change of temperature, viscosity, and so on, to be close to each other, and then taking the difference between both the oscillation frequencies.

In addition, when the proliferation of the putrefactive bacteria proceeds exponentially, the concentration of putrefactive bacteria in the culture medium solution increases, precipitation of the putrefactive bacteria on the blocking layer 12 or the like occurs, and the putrefactive bacteria precipitated on the second vibration area 20b also begins to proliferate. As a result, as illustrated in the period described as "proliferate also in the second vibration area 20b" in FIG. 13(a), there may be a case where the oscillation frequency on the second vibration area 20b side begins to decrease. However, as already described, the oscillation frequency on the second vibration area 20b side barely changes in the period until proliferation of the putrefactive bacteria is observed in this area 20b (equivalent to the periods "putrefactive bacteria absorbed" and "putrefactive bacteria proliferate" in FIG. 13(a)). Therefore, measurement of the presence of putrefactive bacteria and the rate of proliferation can be performed properly by using data obtained in these periods.

When the putrefactive bacteria contained in the sample solution are dead, the oscillation frequency of the first vibration area 20a decreases in the period described as "putrefactive bacteria absorbed" as illustrated in FIG. 13(b). However, these putrefactive bacteria do not proliferate, and thus the oscillation frequency of the first vibration area 20a does not change any further. Accompanying that the putrefactive bacteria are hardly absorbed, the oscillation frequency of the second vibration area 2b stays at a constant value. Also in such a case, a change in oscillation frequency due to environmental changes can be cancelled out by taking the absolute value of the difference in oscillation frequencies obtained from the first, second vibration areas 20a, 20b.

In the microorganism detecting apparatus 70 according to the second embodiment, the crystal resonator 2a provided with the antibody layer 11 is disposed in the incubator 700, the sample solution is supplied to this incubator 700, and the presence of microorganisms which are the detection targets and the rate of proliferation of microorganisms are detected based on a change in oscillation frequency of the crystal resonator 2 provided with the antibody layer 11. By conventionally performed approaches to observe microorganisms such as bacteria which are made to proliferate in an agar medium with a microscope or the like, a test period of about three days to one week for example is required for finding the presence of microorganisms and the rate of proliferation. In this aspect, a method for detecting microorganisms using a piezoelectric vibrator such as the crystal resonator 2a has high sensitivity, and is capable of detecting a mass change of a quite small amount, such as nanograms. Accordingly, it is not necessary to wait for proliferation of microorganisms until it can be observed optically, and it becomes possible to detect the presence of the detection targets and the rate of proliferation by a much shorter period of time than by conventional methods, such as 10 hours to two days.

Further, in this method using the crystal resonator 2a with high sensitivity, the influence of environmental changes, such as a change in ambient temperature of the crystal resonator 2a and changes in temperature and viscosity of liquid (sample solution or culture medium solution) in contact with the crystal resonator 2a, on the oscillation frequency of the crystal resonator 2a becomes large. Here, the microorganism detecting apparatus 70 according to the second embodiment uses the crystal resonator 2a having the first vibration area 20a for detecting microorganisms which is provided with the antibody layer 11 for absorbing microorganisms, and the second vibration area 20b for reference which is not allowed to absorb microorganisms. Accordingly, by taking the difference in oscillation frequencies obtained from both the vibration areas 20a, 20b, it is possible to cancel out the influence of the environmental changes, thereby allowing to properly grasp a change in oscillation frequency due to absorption of microorganisms.

Here, it is possible to replace the components of the incubating apparatus described in the first embodiment and the microorganism detecting apparatus 70 described in the second embodiment appropriately as necessary. For example, the heater 60 used in the first embodiment may be provided in the microorganism detecting apparatus 70 of the second embodiment, or conversely the incubator 7 of the first embodiment may be disposed in the constant temperature chamber 706. Moreover, the microorganism detecting apparatus 70 of the second embodiment, which is of what is called flow injection type, may be structured as a batch type similarly to the incubator 7 according to the first embodiment. In this case, for example, the crystal resonator 2a on which a sample solution is applied in advance is disposed in the antibody layer 11 in the incubator 700 which is not provided with the supply port 704 and the discharge port 705, the culture medium solution is supplied thereafter to the inside of the incubator 700 and then the support body 71 is covered with the cover 81, and the inside of the incubator 700 is adjusted at a preset temperature, thereby performing detection of microorganisms. Besides this, a piezoelectric sensor (hereinafter referred to as a twin sensor) using the crystal resonator 2a having the first vibration area 20a for detecting microorganisms and the second vibration area 20b for reference may be used in the incubation apparatus according to the first embodiment. Conversely, when the influence of environmental changes would not be a problem, the crystal resonator 2 described in FIG. 2 in which the vibration area 20b for reference is not provided may be used instead of the twin sensor in the microorganism detecting apparatus 70 according to the second embodiment.

What is claimed is:

1. A method of using a detecting apparatus that detects detection targets by obtaining at least one of presence of microorganisms and a rate of proliferation of microorganisms based on a change over time in an oscillation frequency of a piezoelectric vibrator, the detecting apparatus comprising:

the piezoelectric vibrator having electrodes formed on both faces, and having an antibody layer formed on the electrode on one face side thereof allowing microorganisms which are detection targets to be absorbed into the antibody layer;

an incubation container comprising an incubation space, to which a sample solution is supplied, for retaining said piezoelectric vibrator, wherein said one face side on which the antibody layer is formed is directed to the incubation space;

a sample solution supply part supplying the incubation container with a sample solution in which are mixed microorganisms which are detection targets having an antigen to be absorbed in the antibody layer through antigen-antibody reaction;

a culture medium supply part supplying the incubation container with a liquid culture medium;

a temperature adjusting part for maintaining said incubation space at a constant temperature;

a supplied-liquid switching part that switches the part connected to said incubation container between said sample supply part and said culture medium supply part; and an oscillation circuit for oscillating the piezoelectric vibrator; and the method comprising:

using the supply liquid switching part to cause the connection destination of the incubation container to be the sample solution supply part, supplying the sample solution to the incubation container;

switching, after said using, the connection destination of the incubation container to the culture medium supply part and supplying liquid culture medium to a surface of the antibody layer where the microorganisms have been absorbed, so as to replace the sample solution with the liquid culture medium;

in a still state wherein supply of the liquid culture medium has been stopped, using, after said switching, the temperature adjustment part to maintain the temperature in the incubation container at a temperature at which the microorganisms that are the detection targets can proliferate, and oscillating the piezoelectric vibrator; and measuring changes in the oscillation frequency of the piezoelectric vibrator that accompanies proliferation of the microorganisms at the interface between the liquid culture medium and the antibody layer.

2. The method of claim 1, wherein the piezoelectric vibrator comprises:

a first vibration area for detecting microorganisms structured by forming electrodes on both faces of the piezoelectric vibrator with the antibody layer being formed on the electrode on one face side thereof; and a second vibration area for reference provided in an area different from the first vibration area via an elastic boundary layer and structured by forming electrodes on both faces of the piezoelectric vibrator; and wherein the antibody layer is not formed on either of the electrodes on the both faces; and wherein a first oscillation circuit oscillates the first vibration area and a second oscillation circuit oscillates the second oscillating area.

3. The method of claim 1, wherein the microorganisms are bacteria and fungi.

4. The method of claim 3, wherein the bacteria and fungi can proliferate under temperature conditions of 50° C. to 70° C.

5. A method of using a detecting apparatus for detecting detection targets by obtaining at least one of presence of microorganisms and a rate of proliferation of microorganisms based on a change over time in an oscillation frequency of a piezoelectric vibrator, the detection apparatus comprising:

the piezoelectric vibrator having electrodes formed on both faces;

an incubation container comprising an incubation space for retaining said piezoelectric vibrator;

a sample solution supply part for the incubation container;

a culture medium supply part for the incubation container;

a temperature adjusting part for maintaining said incubation space at a temperature;

a supplied-liquid switching part that switches a part connected to said incubation container between said sample solution supply part and said culture medium supply part; and an oscillation circuit for oscillating the piezoelectric vibrator; and the method comprising:

forming an antibody layer on a face side of an electrode of the piezoelectric vibrator;

supplying to an incubation container a sample solution in which are mixed microorganisms which are detection targets having an antigen to be absorbed in the antibody layer through antigen-antibody reaction, wherein a face side on which the antibody layer is formed is directed to an incubation space;

switching supply of the incubation container from said sample solution to a liquid culture medium to supply said liquid culture medium to a surface of the antibody layer where the microorganisms have been absorbed, so as to replace the sample solution with the liquid culture medium;

maintaining said incubation space at a constant temperature at which the microorganisms that are the detection targets can proliferate;

oscillating the piezoelectric vibrator; and measuring changes in the oscillation frequency of the piezoelectric vibrator that accompanies proliferation of the microorganisms at an interface between the liquid culture medium and the antibody layer.

* * * * *